United States Patent [19]

Kay

[11] Patent Number: 4,668,227
[45] Date of Patent: May 26, 1987

[54] STOMA HYGIENE SYSTEM AND PROCESS THEREFOR

[76] Inventor: Dennis M. Kay, Suite D 3302 U.S. Alt. 19 North, Palm Harbor, Fla. 33563

[21] Appl. No.: 731,897

[22] Filed: May 8, 1985

[51] Int. Cl.$^4$ ............................................ A61M 35/00
[52] U.S. Cl. ................................. 604/289; 604/277; 604/334; 134/57 R; 134/95; 134/98; 4/420.1; 4/516; 4/661
[58] Field of Search ............................. 604/150–153, 604/118, 121, 275–279, 73, 289, 334; 4/420.1–420.5, 443–448, 515–519, 661; 134/57 R, 95, 58 R, 98

[56] References Cited

U.S. PATENT DOCUMENTS

| | | | |
|---|---|---|---|
| 3,044,465 | 7/1962 | Anderson et al. | 604/150 |
| 3,057,352 | 10/1962 | McKenna | 604/275 |
| 3,916,924 | 11/1975 | McGowan | 134/95 |
| 3,993,054 | 11/1976 | Newman | 604/153 |
| 4,134,404 | 1/1979 | Williams, Jr. | 604/277 |
| 4,167,193 | 9/1979 | Magnus et al. | 134/95 |
| 4,194,506 | 3/1980 | Voorhies | 604/334 |
| 4,278,078 | 7/1981 | Smith | 604/153 |
| 4,281,674 | 8/1981 | Tanaka et al. | 134/95 |
| 4,559,036 | 12/1985 | Wunsch | 604/250 |

Primary Examiner—Dalton L. Truluck
Assistant Examiner—Mario Costantino
Attorney, Agent, or Firm—Lalos, Keegan & Kaye

[57] ABSTRACT

Cleansing equipment and a daily process for cleansing an ostomy faceplate and the peristomal area while on the ostomate's body. This equipment and process are intended to reduce the occurrence of infections in long-term ostomates. Pressurized fluids delivered through a specially configured nozzle and premoistened antiseptic swabs are used to dislodge, rinse and remove bacteria and bacterial growth medium from the corresponding faceplate surfaces and peristomal areas. The hygiene unit accomplishes this cleansing process by pumping water and cleansing fluids in an orderly predetermined sequence at the required flow rates, volumes, composition and pulse frequencies. Special adapters permit the hygiene unit nozzle to connect with and cleanse ostomy appliance receptacles and urinary drainage systems. The hygiene unit is equipped with a "clean" function so that it can clean itself. It further is designed so that excessive fluid flow rates are not pumped while cleansing the peristomal area and so that it safely shuts itself off when its fluid reservoirs are empty.

23 Claims, 20 Drawing Figures

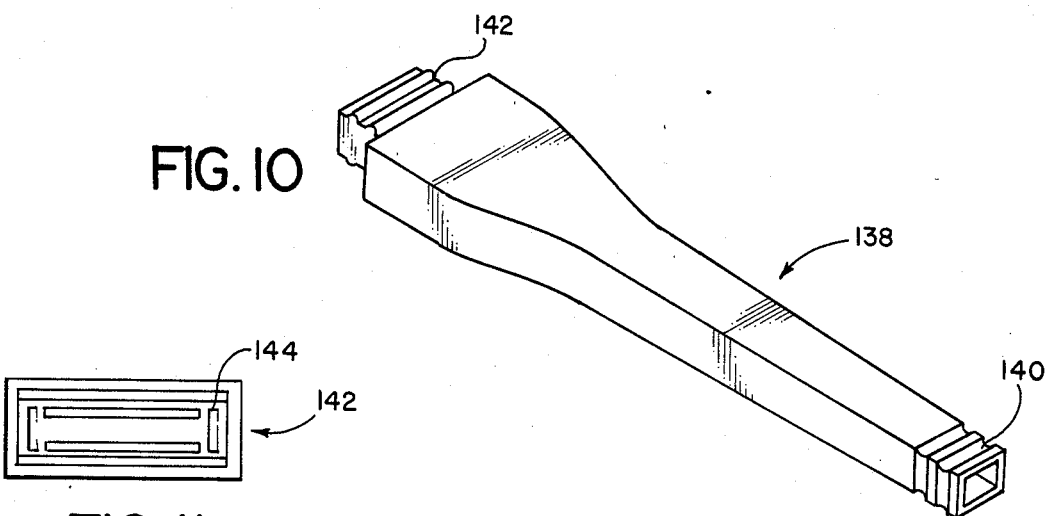
FIG. 10
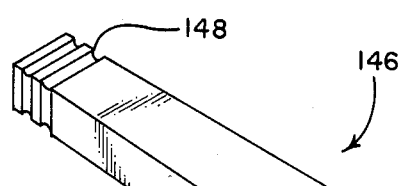
FIG. 11
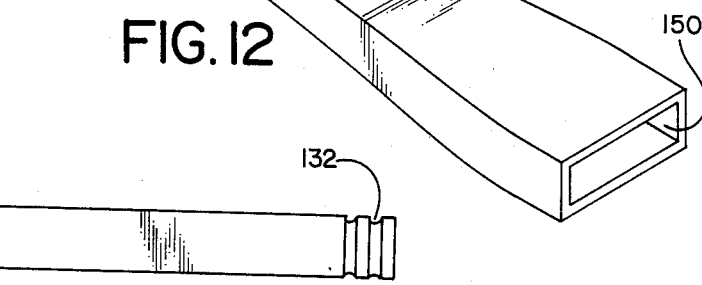
FIG. 12
FIG. 13
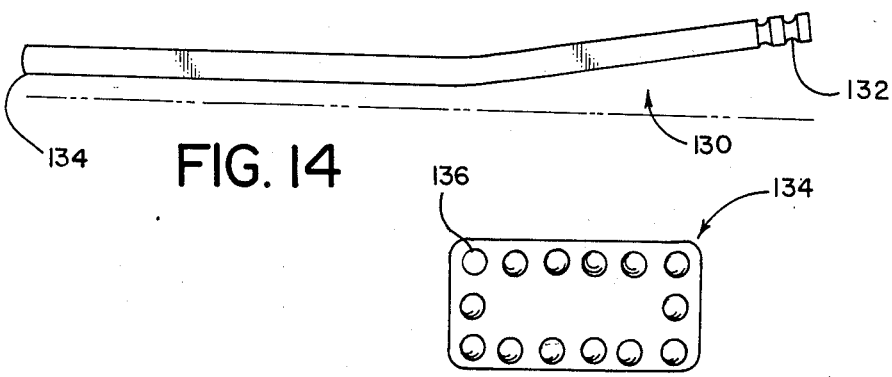
FIG. 14
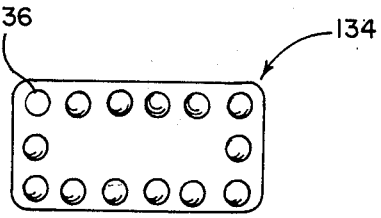
FIG. 15

STOMA HYGIENE SYSTEM AND PROCESS THEREFOR

BACKGROUND OF THE INVENTION

The present invention relates to ostomy appliances and more particularly to urostomy appliances, including urostomy faceplates and receptacles. It also relates to hygiene and cleansing procedures and equipment for urostomates.

Chronic or recurrent infections are one of the leading causes of morbidity or illness in long-term ostomates, especially those with urinary diversions. All types of urostomies excrete mucus with the urinary wastes. This mucus tends to accumulate around the stoma and on the adjacent faceplate where in the presence of urine and body heat, an excellent medium for bacterial growth is created. Current ostomy products do not provide for easy access to the stoma for proper hygiene and prevention of these infections. Additionally, no process or program for effective stoma care, cleansing or disinfecting is known.

OBJECT OF THE INVENTION

Accordingly, it is the principal object of the present invention to provide a novel hygiene system for urostomates.

Another object is to provide novel cleansing equipment for ostomy appliances.

A further object is to provide an improved urostomy cleaning method that reduces infections in urostomes.

A still further object is to provide a novel arrangement that provides access to the peristomal areas for cleansing while the faceplate is on the urostomate's body.

Another object is to provide a novel assembly for cleansing ostomy receptacles and urinary drainage systems.

Other objects and advantages of the present invention will become more apparent to those persons having ordinary skill in the art to which the present invention pertains from the following description taken in conjunction with the accompanying drawings.

DESCRIPTION OF THE DRAWINGS

FIG. 10 is a perspective view of a receptacle cleansing adapter of the present invention.

FIG. 11 is a left end view of the adapter of FIG. 10.

FIG. 12 is a perspective view of a urinary drainage system cleansing adapter of the present invention.

FIG. 13 is a top view of an outflow channel cleansing nozzle of the present invention.

FIG. 14 is a side view of the nozzle of FIG. 13.

FIG. 15 is an enlarged end view of the tip of the nozzle of FIG. 13.

DESCRIPTION OF THE INVENTION

Description of the Stoma Hygiene Equipment

Figure 17:
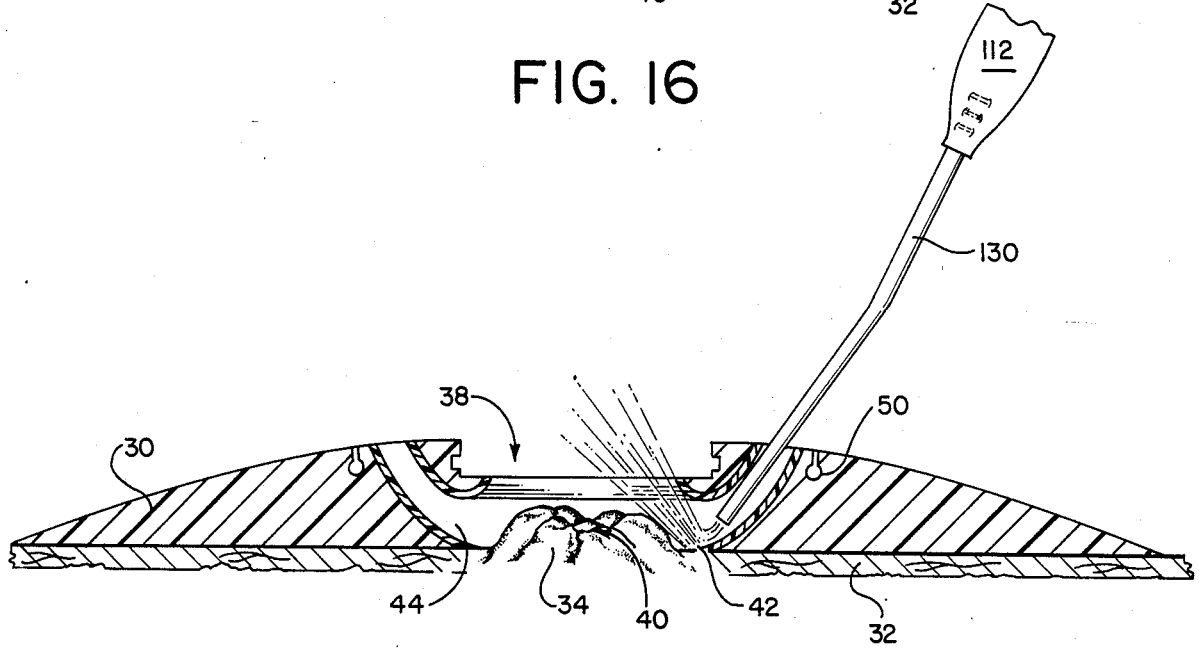
FIG. 17 is a view similar to FIG. 16 illustrating the removal step of the present invention.
Figure 18:
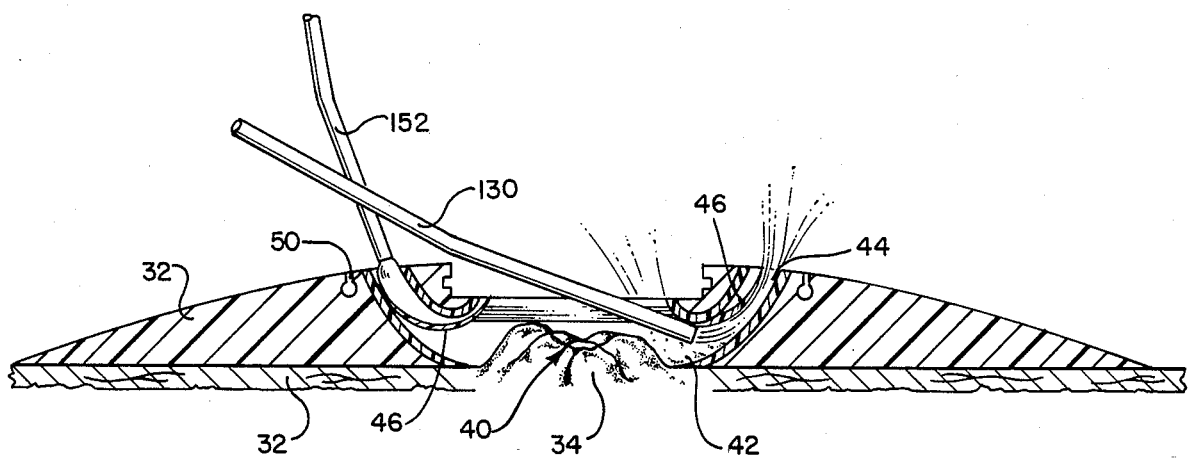
FIG. 18 is a view similar to FIG. 16 illustrating the dislodging step on a faceplate having one-way channel valves.
Figure 19:
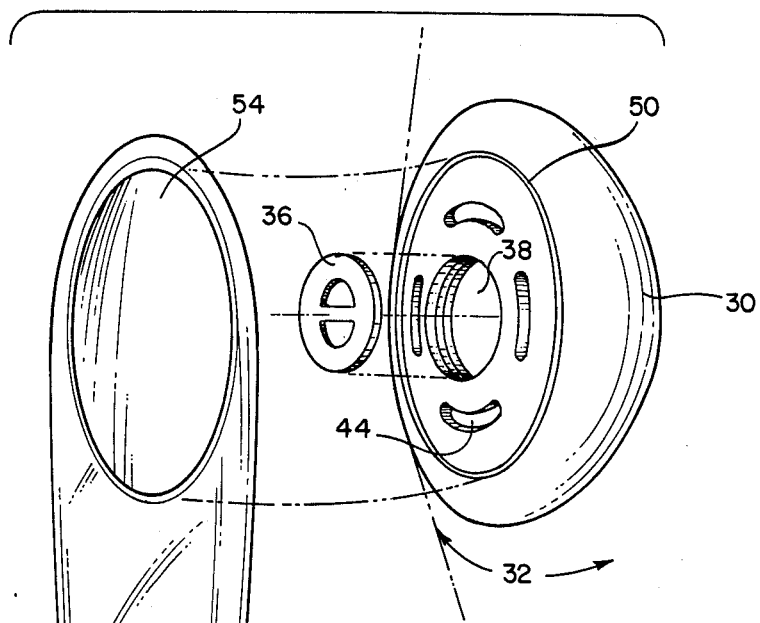
FIG. 19 is a perspective view of a urostomy appliance illustrating the disassembling step of the present invention.

The present invention provides for a novel method and regimen for the daily cleansing of the external stoma area as well as the cleansing of ostomy appliance equipment, which is illustrated generally in FIG. 19. The equipment includes a faceplate 30 positionable against the urostomate's skin 32 over his stoma 34, as is best shown in FIGS. 9 and 16 through 18. A removable stoma faceplate shield 36 screws into and out of a central opening 38 in faceplate 30 as shown in FIG. 19. For normal use, shield 36 is screwed into position in faceplate 30 to provide protection for the stoma 34 should an article directly impact the faceplate over the stoma. This is better and more fully described in applicant's co-pending application, Ser. No. 665,449, filed Oct. 26, 1984, the contents of which are hereby incorporated by reference in their entirety.

Protector shield 36 can be readily unscrewed, by grasping and turning its handle, and then removed from faceplate 30. A central opening or channel 38 directly over stoma 34 is thereby defined by ease of directly cleansing the area around the stoma, the peristomal area 42.

A plurality of faceplate channels 44 spaced from central opening 38 and encircling stoma 34 provide for outflow of bodily waste products from stoma 34 through faceplate 30 to receptacle 48 while entire ostomy appliance is assembled and in use on body 32. As will be described more fully later, during the cleansing process, pressurized fluids can then be inserted through either channel 44 or the protector shield opening 38, or both, and reflected or splashed out of the same or the adjacent opening or channel to cleanse the peristomal area 44 and the adjacent faceplate of bacteria and bacterial growth medium. One-way flap valves 46 can be mounted in the channels 44, as shown in FIG. 18, to prevent the urinary waste fluids from freely refluxing back through these outflow channels 44 and into the stoma, while the urostomy appliance is in use.

Figure 20:
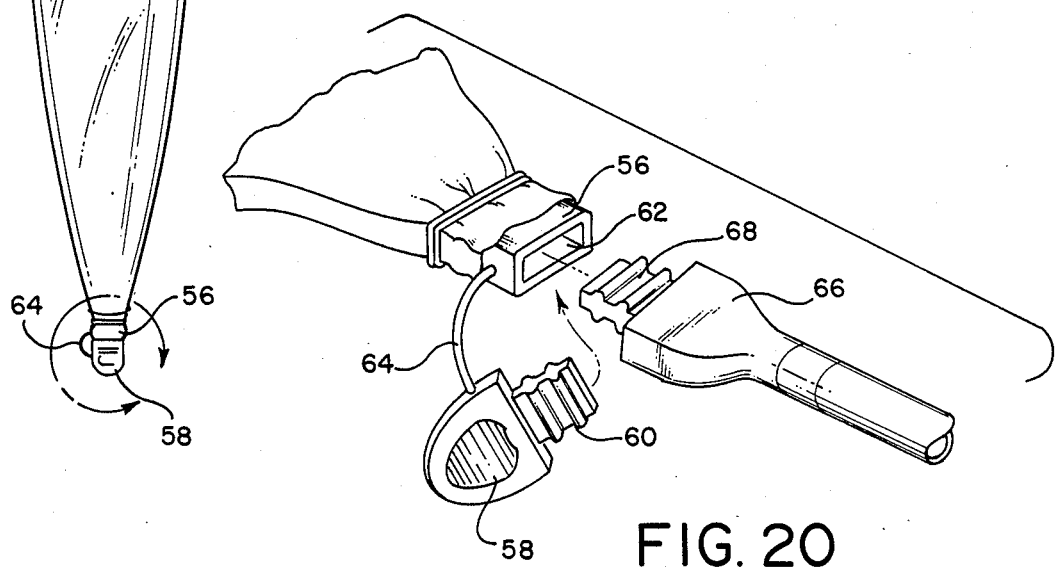
FIG. 20 is an enlarged perspective of the drain valve of FIG. 19 illustrated in its disconnected position relative to a urinary drainage connector member.

The appliance receptacle 48 for collecting the urinary waste material is secured to the outside face of faceplate 30. As shown in FIG. 19, a system can be provided with a groove 50 encircling the outer channels and a corresponding mated circular rib member 52 encirciling the receptacle opening 54. Rib member 52 can then be easily and readily snapped into or out of groove 50 to attach or detach receptacle 48 from faceplate 30, even while faceplate 30 is on the urostomate's body 32. A drain valve 56 and removable plug 58 are positioned at the opposite end of receptacle 48 for draining the receptacle. As best shown in FIG. 20, removable plug 58 has a double acting, lock male member 60 which fits into the female member 62 of receptacle drain valve 56. The plug is conveniently secured to the outside of the valve by a lanyard 64. For night or bedside drainage, a connector member 66 is provided, which includes a male connector 68 also adapted to fit into female member 62 of valve when plug 58 has been removed. A drain hose 68 exits from the rear of connector member 66 for draining the urinary waste from the receptacle 48 to a suitable collection cannister (not shown). This canister and drainage system are more fully described in applicant's co-pending application, Ser. No. 665,450 filed Oct. 26, 1984, the contents of which are hereby incorporated by reference in their entirety.

Figure 1:
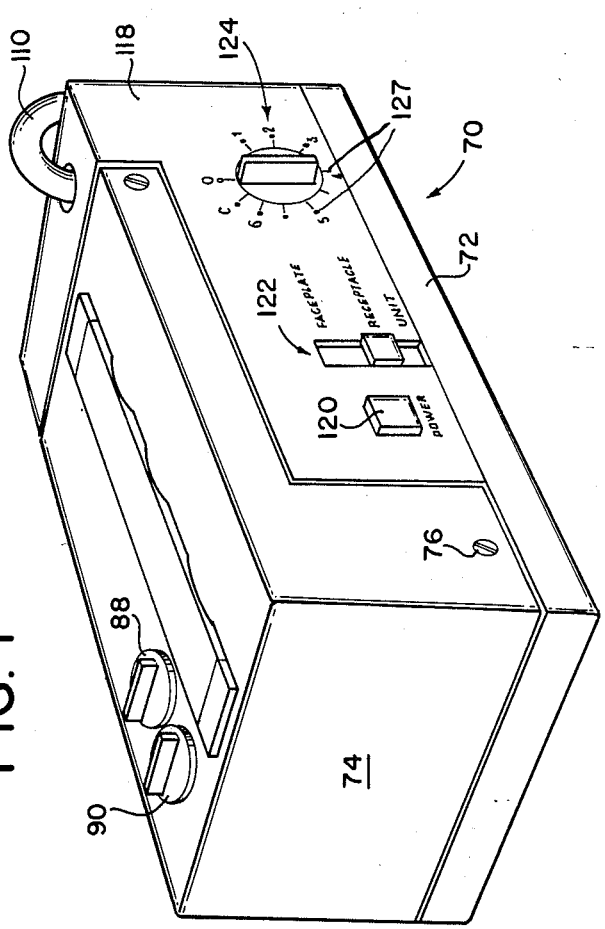
FIG. 1 is a perspective view of stoma hygiene unit of the present invention.
Figure 3:
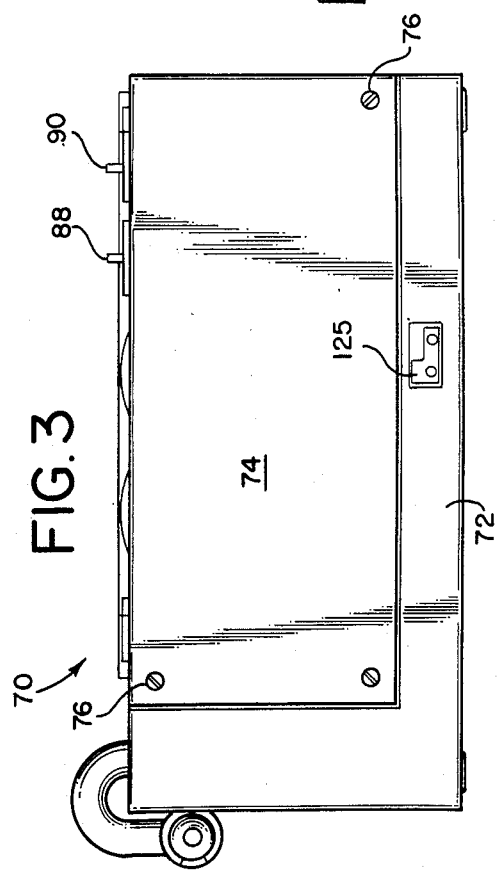
FIG. 3 is a rear view of the unit of FIG. 1.
Figure 4:
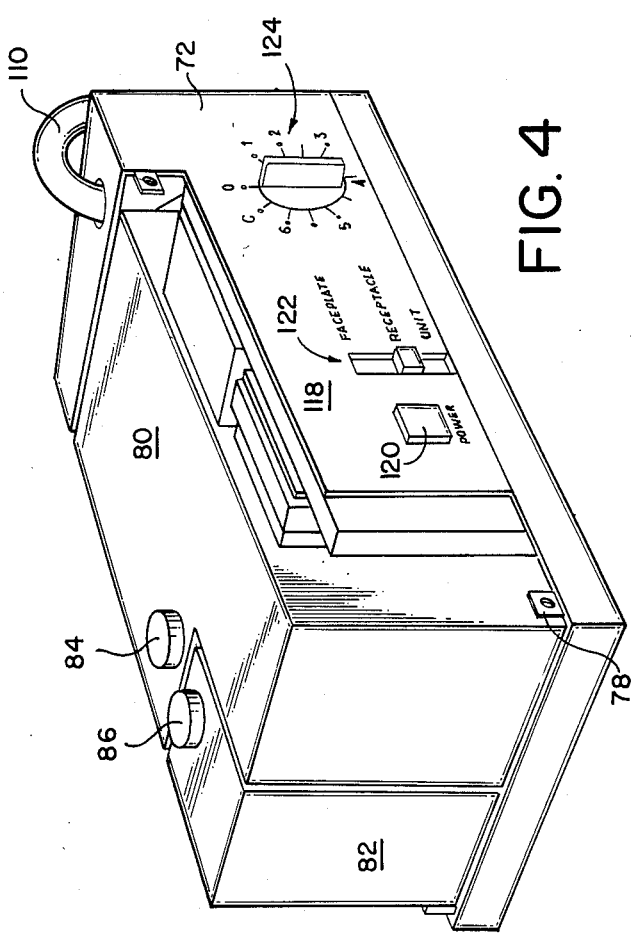
FIG. 4 is a perspective view of the unit of FIG. 1 with external housing removed.

A specially-designed electrically powered stoma hygiene unit shown generally at 70 in FIG. 1 pumps pressurized fluids at the desired fluid compositions, fluid flow rates, volumes, and pulse rates to cleanse peristomal area 42 and the ostomy appliance equipment. Hygiene unit 70 comprises a base unit 72 and an external housing 74 secured to the base unit by a plurality of nylon screws 76 inserted through corresponding base unit threaded tabs 78.

Figure 2:
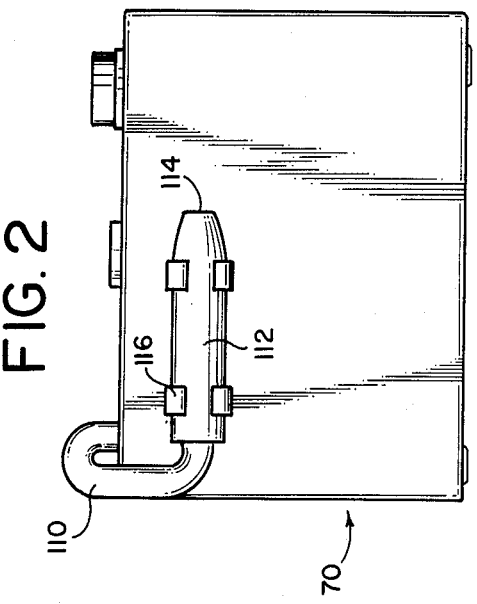
FIG. 2 is a side view of the unit of FIG. 1.
Figure 5:
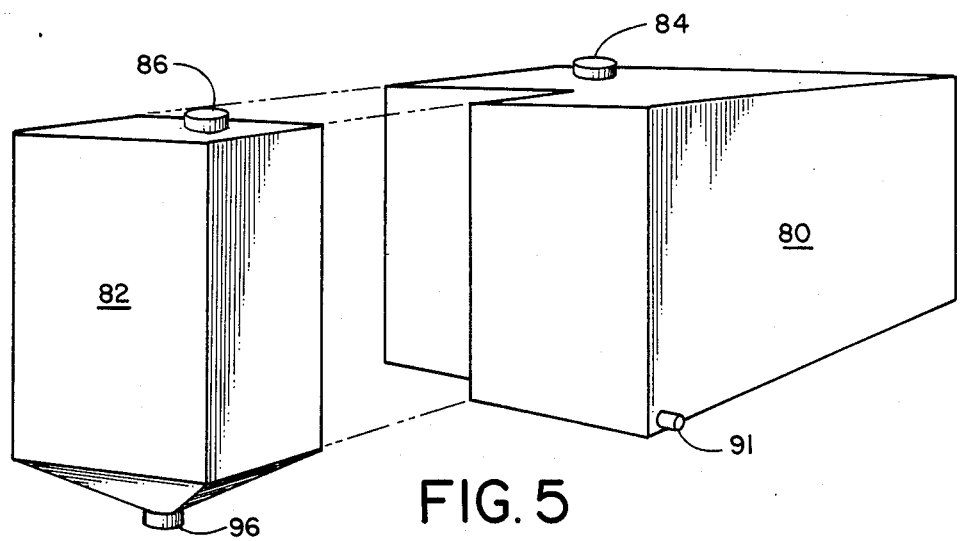
FIG. 5 is a perspective view of the reservoirs of the unit of FIG. 1.
Figure 6:
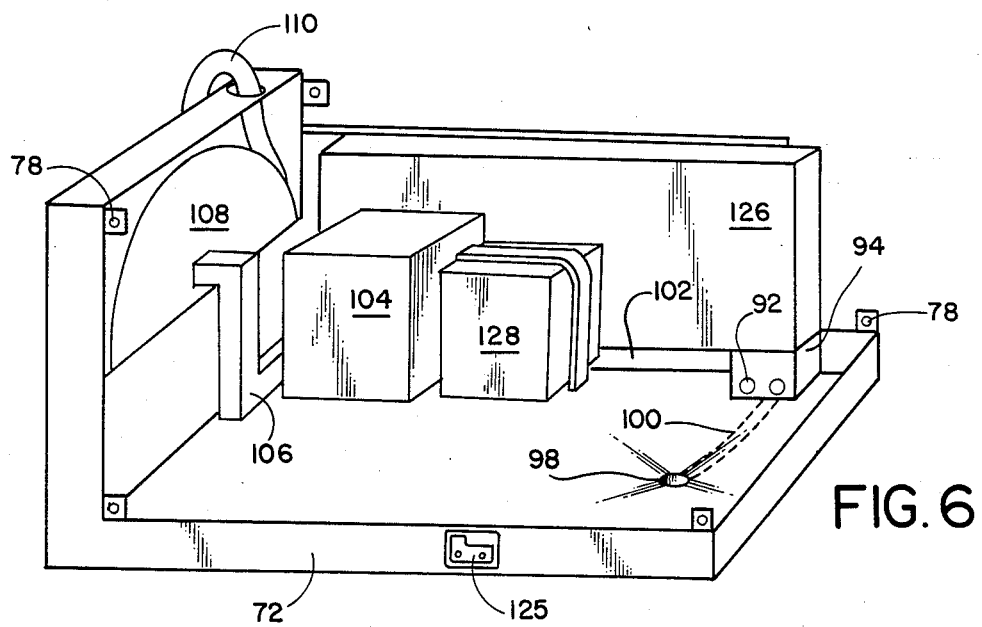
FIG. 6 is a perspective view of the rear of the unit of FIG. 1 with the external housing and reservoirs removed.

Base unit 72 supports a one thousand milliliter water reservoir 80 and a one hundred and twenty-five milliliter cleansing solution reservoir 82 designed to hold a ten percent povidone-iodine solution. The reservoirs are nested together on base unit 72 as best shown in FIG. 5, and each has its own filling port 84 and 86, respectively, with threaded port plugs 88 and 90. Water reservoir 80 has a discharge port 91 exiting from the side thereof into the female port 92 of an electrically actuated Y valve 94. Cleansing solution reservoir 82 communicates with the Y valve 94 via a male discharge port 96 which plugs into a drain 98, shown in FIG. 6, which in turn communicates with a tube 100 that extends to Y valve 94. A single plastic tube 102 then communicates Y valve 94 with the fluid pump 104. The Y valve determines which of the reservoirs will communicate with fluid pump 104 and thereby from which reservoir fluid pump 104 will pump the fluid out through the outflow tube 106 to a spring loaded outflow hose reel 108. Outflow hose reel 108 is similarly configured and operates like the reel of Ser. No. 665,450. It keeps the outflow hose 110 from tangling and automatically winds the excess hose about the reel. An external nozzle handle 112 is secured to the outer end of outflow hose 110 to provide a grasping surface as well as a female connector member 114 for the different adapters and nozzles. As shown in FIG. 2, suitable nozzle handle retaining clips 116 are secured to the outside of base unit 72 for easy storage of nozzle handle 112 when hygiene unit 70 is not being used.

Additionally, mounted on the front plate 118 of base unit 72 are the on power button 120, the function selector switch 122, and the step selector dial 124; all control the operations of the hygiene unit as will be later described. Step selector dial 124 indicates the orderly progression through the hygiene steps. Each position of the step selector dial has a corresponding light emitting diode (LED) indicator 127 visible on the front plate 118, and arranged in respective clockwise display around the dial. A suitable jack receptacle 125 is mounted on the back of the base unit for connecting it to a power source. A control unit or microprocessor 126 is electrically connected to the electric motor 128 which drives and controls fluid pump 104 and controls its pumping characteristics. The microprocessor control unit 126 also controls the Y valve 94 to determine from which of the reservoirs 80 or 82, fluid pump 104 will pump the fluid out through outflow hose 110. Thus the microprocessor 126 operates as an "on-board computer", controlling and monitoring the accuracy, progression, timing and completion of all of the unit's functions. The hygiene unit, as an additional precaution, requires coordination between function selector switch 122 and step selector dial 124 to prevent excessive fluid flow rates while cleansing peristomal areas.

For inserting pressurized fluids pumped by fluid pump 104 of hygiene unit 70 into outflow channels 44 or faceplate opening 38, a special outflow channel nozzle is used and is best shown generally at 130 in FIGS. 13 through 15. At one end thereof, a double notched lock 132 is provided for inserting and securing outflow channel nozzle 130 into female connector member 114. The opposite tip end 134 has a width and a height to conform to the dimensions and configurations of the inner opening of the outflow channel near the stoma. Also, as best shown in FIG. 15, the front tip 134 has a series of peripheral ports 136 for directing the flow of cleansing solution along the inner surface of the outflow channel.

The receptacle cleansing adapter of the preesent stoma hygiene system is illustrated generally at 138 in FIGS. 10 and 11. It has at one end an attachment 140 compatible with female connector member 114 of the cleansing nozzle handle, and is secured in member 114 by a double notch lock mechanism. At the adapter's opposite end, a double locking plug seal 142 is provided that is compatible with the appliance drain valve 62 as illustrated in FIG. 20. The adapter's double locking plug seal end 142 also has a series of peripheral ports 144, best illustrated in FIG. 11. These ports provide the optimum fluid flow for cleansing the inner surfaces of the drain valves and receptacles. Similarly, a urinary drainage system cleansing adapter, as illustrated generally at 146 in FIG. 12, is used for cleansing the urinary drainage system. This urinary drainage system cleansing adapter has at one end an attachment 148 compatible with connecting member 114 of the cleansing nozzle handle and a female type connector 150 at its opposite end that is compatible with the double locking plug 68 of connector member 66 of FIG. 20.

Figure 7:
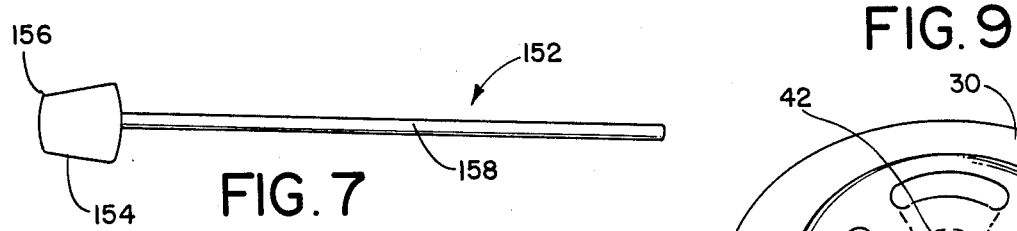
FIG. 7 is a top view of a swab of the present invention.
Figure 8:
FIG. 8 is a side view of the swab of FIG. 7.
Figure 9:
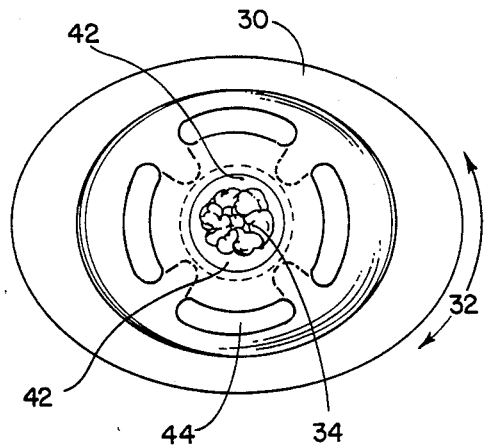
FIG. 9 is a top plan view of a faceplate in place on the urostomate with the faceplate shield removed as preparation for cleansing pursuant to the methods of the present invention.

Specially designed, and individually packaged swabs are illustrated generally at 152 in FIGS. 7 and 8. Each has a swab member 154 made of soft synthetic porous absorbent sterile material and saturated with an antiseptic solution, such as ten percent povidone-iodine solution. As best shown in FIG. 7, swab member 154 is shaped so that its broadest dimension easily conforms with the inner (nearest to the stoma) aspect of outflow channel 44. The tip 156 of swab member 154 is pointed to best access the area between the peristomal skin 42 and the inner edge of the faceplate stoma opening. An elongated flexible, but stiff, plastic handle 158 is attached to swab member 154. As shown in FIG. 8, it is bent approximately ten degrees in a middle location to provide better channel access.

Description of the Hygiene Process

Figure 16:
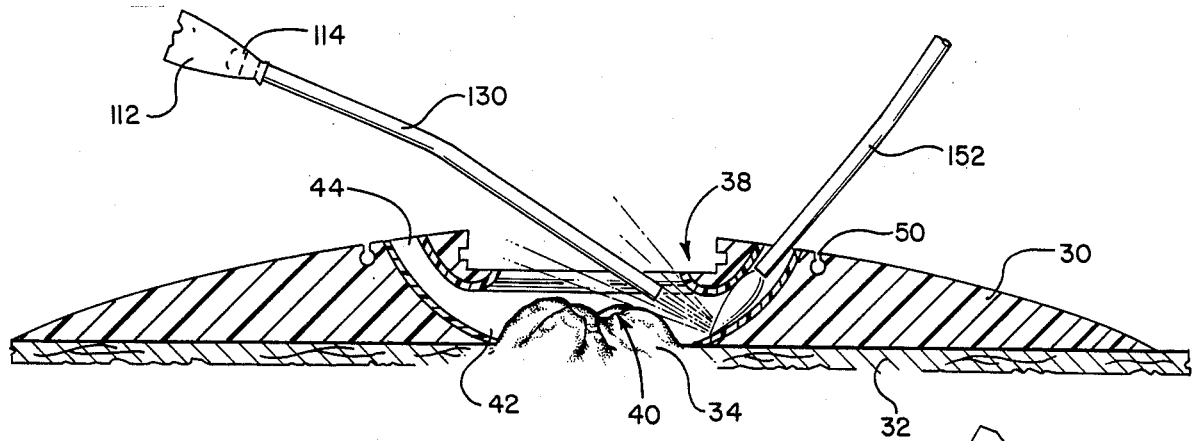
FIG. 16 is an enlarged cross-sectional view of a faceplate in place around the stoma, on the user, illustrating the dislodging step of the present invention.

The following is a description of a daily regimen process of peristomal and faceplate hygiene, as performed using stoma hygiene unit 70 while faceplate 30 is in place on the urostomate's body, and receptacle 48 and faceplate stoma protector shield 36 are removed from the faceplate. Stoma shield 36 can be cleansed during this process and the removed ostomy appliance receptacle 48 is cleansed pursuant to a process described later. It is emphasized that care is taken at all times to avoid direction of the flow of cleaning solution of water directly into the stoma opening 40. Referring to FIGS. 16, 17, and 18, the cleansing of faceplate 30 and peristomal area 42 is accomplished in three steps, as follows:

Step One: Five Hundred Milliliters of clean tap water flowing at approximately fifteen pounds per square inch are directed toward the external surfaces of faceplate 30 and peristomal areas 42, using the cleansing nozzle 130. During this first step, the water flow is without pulsation and is used in combination with sterile swabs 152 to dislodge mucus, bacteria and bodily wastes from the surfaces of the faceplate and peristomal areas. It is also within the scope of the present invention to use pressurized gas to help dislodge the bacteria growth medium.

Step Two: The external surfaces of faceplate 30 and peristomal area 42 including the removed stoma shield 36 are cleansed with one hundred twenty-five milliliters of ten percent povidoneiodine solution, flowing through the cleansing nozzle 130 at approximately twenty pounds per square inch with a pulsating flow at a frequency of approximately two to four cycles per second. After the completion of step two there is a five minute pause to allow maximal antibacterial action of the povidone-iodine solution.

Step Three: The external surfaces of the faceplate 30, the removed stoma shield 36 and the peristomal areas 42 are then rinsed with five hundred milliliters of clean tap water flowing at a rate of approximately twenty-five pounds per square inch using a pulsating flow at a frequency of two or four cycles per second. Throughout this entire faceplate and peristomal hygiene process, care is taken with swabs 152 and cleansing nozzles 130 to gently reach all peristomal areas 42, and all external portions of the faceplate 30 that are exposed to bodily wastes. To avoid introduction of foreign materials or bacteria into the body, the cleansing swabs 152 flow of cleansing solution or water, are never introduced directly into stoma opening 40.

Referring to FIGS. 16, 17 and 18, it is demonstrated in cross section that faceplate 30 when in place around stoma 34, is flush to the wearer's skin at all points around the stoma. The appliance receptacle 48 and faceplate stoma shield 36 have been removed in preparation for the cleansing process, with the faceplate still in place on the wearer. There is no space or potential space between the patient's skin and the faceplate, except directly over the stoma. Since there is no potential space between faceplate 30 and the urostomate's adjacent body, cleansing fluids are never deposited between faceplate 30 and the urostomate's adjacent body 32 and therefore no means of removal of these fluids is required. Fluids used during the cleansing process simply splash off the faceplate surfaces and peristomal areas, without being trapped or contained. FIG. 16 demonstrates the use of the cleansing swab 152 and cleansing nozzle 130 as they would be used during step one of the cleansing process. As shown, cleansing nozzle 130 is inserted through the removed shield opening 38 or channel 44 and water flows agasint the peristomal area and splashes back out through the opening 38. FIG. 17 demonstrates the use of the cleansing nozzle during step two of the faceplate cleansing process. The nozzle is inserted through one of the channels 44, and the cleansing solution flows out against the peristomal area and splashes out through the shield opening 38. FIG. 18 demonstrates the use of cleansing nozzle 130 and swab 152 during step one of the cleansing process of faceplate 30 equipped with a one-way flap valve 46 in outflow channels 44. Swab 152 cleans between flap valve 46 and the wall of the outflow channel 44 at the flap valve attachment. The cleansing nozzle 130 inserted through shield opening 38 cleanses the proximal portion of outflow channel 44. The brisk flow of fluid from the nozzle causes flap valve 46 to open and fluid rushes out of the outflow channel. The present faceplates can also be easily removed from the urostomate's skin and cleansed after removal. In all cases, however, cleansing swab 152, the cleansing nozzle 130 and the stream of cleansing fluid are never aimed at or place directly through the stoma opening 40 or into the user's body.

The cleansing of ostomy appliance receptacle 48 and drain valve 56 or other ostomy equipment when removed from the user's body also comprises three basic steps, which are designated as steps four, five and six, respectively.

Step four: With ostomy appliance receptacle 48 removed from faceplate 30, the receptacle is attached to the cleansing nozzle 138 by mating the nozzle to the open or unplugged drain valve 56 at the distal end of receptacle 48. After attaching the drain valve 56 to the stoma hygiene unit, the receptacle 48 is rinsed with five-hundred milliliters of clean tap water flowing at approximately forty pounds per square inch, using a pulsating flow at a frequency of approximately four cycles per second.

Step Five: The receptacle 48 drain valve 56 assembly, still attached to cleansing unit 70, is next rinsed with one hundred twenty-five milliliters of ten percent povidone-iodine solution flowing at a rate of approximately forty pounds per square inch, using a pulsating flow at a frequency of approximately four cycles per second. After step five a pause of five minutes is required to allow maximal antibacterial action of the povidone-iodine solution.

Step Six: The drain valve and receptacle assembly is rinsed with five hundred milliliters of clean tap water with a flow rate of approximately forty pounds per square inch, using a pulsating flow at a frequency of approximately four cycles per second. Prior to reattachment of receptacle 48 to faceplate 30, drain valve plug 58 is cleansed using two hundred milliliters of clean tap water and premoistened sterile swabs 152.

Description of the Hygiene Unit Operating Process

1. The fluid reservoirs 80, 82 are first filled prior to plugging the unit in or engaging the power button 120. Hygiene unit 70 is then plugged into a standard 110 V AC outlet via a usual plug and wire power cord assembly attached to jack receptacle 125 at the back of the unit.

2. Spring-loaded power button 120 is placed in its depressed or "on" position. The circuit is completed between power source and indicator light in power button, causing the button to glow red. Each of six cleansing steps described above and each of the pause positions between steps two and three and steps five and six have corresponding light emitting diode (LED) indicators 127 arranged sequentially around dial 124. Each indicator 127 flashes when unit 70, as determined by the microprocessor 126, is ready to go to the dial position that corresponds to that flashing indicator. When the step selector dial 124 is turned to the position with a flashing indicator, microprocessor 126 notes this and initiates the function of the hygiene step corresponding to the respective indicator. The LED indicator for a step in progress glows constantly (no longer flashing) and then goes off at the completion of that step. When the indicator for the dial position whose step is in progress goes off, this indicates the function corresponding to that dial position has been completed. Immediately thereafter the indicator for the next step will begin flashing until the dial is manually turned to that next step, causing the indicator to glow constantly at the new dial position, corresponding to the new step in progress.

When the main power button 120 is placed in the "on" position the circuit is completed between the power source and microprocessor 126, that controls all functions and steps of hygiene unit 70, as determined by its software program. When microprocessor 126 initially receives power, its program automatically cuases the LED indicator corresponding to the "off" position on the step selector dial 124 to flash. If or when the step selector dial is then placed in the "off" position (corresponding to the flashing indicator), a circuit back to microprocessor 126 is completed, indicating the position of selector dial 124. Microprocessor 126 then completes a circuit to function selector switch 122 and causes the "off" position indicator of the step selector dial to glow constantly, indicating that the circuit to the function selector switch 122 has been completed.

The unit is now ready for function selection. If function selector switch 122 is placed in the "faceplate" position, a signal is sent to microprocessor 126, when then causes the LED indicator corresponding to step one to begin flashing. If the function selector switch 122 is placed in the "receptacle" position, a signal is sent to microprocessor 126 and the portion, a signal is sent to microprocessor 126 and the microprocessor in turn causes the LED indicator corresponding to step four to begin flashing.

The progression of steps through the hygiene process will now be described with regard to the electronic function of the hygiene unit 70.

Step selector dial 124 is equipped with an internal cog wheel and ratchet assembly (not shown) that permits the dial to be manually turned, only in a clockwise direction. An alternative embodiment utilizes a step selector dial 124 that is turned automatically to the correct position using transistors in a transistor level logic electronic sequence circuit. Discussion here will consider operation of the manual step selector dial embodiment. Microprocessor 126 will only initiate the next appropriate step in the hygiene process and will not do so until step selector dial 124 is turned to the appropriate corresponding position with a flashing indicator.

3. Function selector switch 122 is placed in the "faceplate" position and the indicator for step one begins flashing, as directed by the microprocessor 126.

When step selector dial 124 is placed at position one, microprocessor 126 receives this information and causes the indicator at position one to glow constantly, indicating the initiation of step one. As step one is initiated, microprocessor 126 senses the position of the Y valve 94 and, if the Y valve is not open to water reservoir 80, it signals the valve actuator of the Y valve to open Y valve 94 for inflow from the water reservoir. The Y valve actuator utilizes a transistor to transistor logic level or other compatible means for control by microprocessor 126.

Subsequently, microprocessor 126 completes the power circuit to the electric motor component 128 of pump 104 and causes it to begin operation at its slowest speed, producing a nozzle outflow of clean water at approximately fifteen pounds per square inch. Microprocessor uses a pump interface control circuit to provide the necessary logic level signals to control pump motor 128. Hygiene unit 70 thereby achieves its required outflow rates and pulsation frequencies. All timing and control functions originate in the microprocessor 126 and will be logged by the microprocessor. The microprocessor via its integral timing circuit notes the time that the electric pump motor 128 begins operation and interrupts the power circuit to the pump after the appropriate time has elapsed to allow the outflow of 500 milliliters of clean water. As microprocessor 126 interrupts the power circuit to electric pump motor 128, step one is completed. The power circuit for the LED indicator for step one is also interrupted and the indicator for step one goes off. Microprocessor 126 initiates a power circuit causing the LED indicator for step two to begin flashing, indicating that step one has been completed and that the hygiene unit is ready to begin step two.

4. To begin step two, step selector dial 124 is placed at position two, the microprocessor receives this information and causes the LED indicator for step two to glow constantly, indicating the initiation of step two. As step two is initiated, microprocessor 126 signals Y valve 94 to close off the outflow from water reservoir 80 and open the outflow from cleansing solution reservoir 82. Subsequently microprocessor 126 completes the power circuit to electric pump motor 128, causing it to operate at the midrange of its three speeds, producing a pulsating nozzle outflow of cleansing solution at approximately twenty pounds per square inch. The microprocessor via its integral timing circuit notes the time that electric pump motor 128 begins operation and interrupts the power circuit to pump motor 128 after tha appropriate time has elapsed to allow the outflow of 125 milliliters of cleansing solution. As microprocessor 126 interrupts the power circuit to electric pump motor 128, step two is completed and the power circuit for the steady glow of the LED indicator for step two is interrupted, causing the LED indicator for step two to extinguish. The microprocessor initiates a power circuit that causes the LED indicator at the mid-position between steps two and three to begin flashing, indicating that step two has been completed and that the unit is ready for the five minute pause between steps two and three. Step selector dial 124 is placed at the pause position between steps two and three, microprocessor 126 receives this information and causes the LED indicator for the pause position between steps two and three to glow constantly. Simultaneously, the timing circuit of microprocessor 126 is activated and the five minute pause between steps two and three is initiated and timed. Regardless of the position of the step selector dial 124, the microprocessor's timing circuit will not allow the initiation of any step until the five minute pause period has elapsed after the completion of step two. When microprocessor 126 receives information from its timing circuit indicating that the five minute pause has elapsed, the power circuit to the LED indicator at the mid-position between steps two and three is interrupted, causing this LED indicator to go off. Simultaneously, the microprocessor's power circuit to the LED indicator for step three is activated and this indicator begins flashing, indicating that the pause period has elapsed and that the unit is ready for step three.

5. To begin step three, step selector dial 124 is placed at position three, microprocessor 126 receives this information and causes the LED indicator for step three to glow constantly, indicating the initiation of step three. As step three is initiated, the microprocessor signals the actuator for the Y valve 94 to close off the outflow from cleansing solution reservoir 82 and open the outflow from water reservoir 80. Subsequently the microprocessor 126 completes the power circuit to electric pump motor 128, causing it to operate at the midrange speed producing a pulsating nozzle outflow of water at approximately twenty pounds per square inch. The microprocessor 126, via its integral timing circuit, then notes the time that electric pump motor 128 begins operation and interrupts the power circuit to this pump after the appropriate time has elapsed to allow the outflow of five hundred milliliters of water. As microprocessor 126 interrupts the power circuit to the electric pump motor, step three is completed and the power circuit for the steady glow of the LED indicator for step three is interrupted, causing the indicator for step three to go off. At the completion of step three, microprocessor 126 initiates a circuit that signals main power button 120 to return to the "off" position. The main power circuit between the power source jack 125 and the main power button 120 is interrupted, turning the entire hygiene unit 70 off, as a reminder to unplug the unit before refilling the reservoirs 80 and 82 for the next cleansing process.

6. Steps four through six with a pause of five minutes between steps five and six proceed in an electronically similar fashion as described above for steps one through three. During steps four through six electric pump motor 128 is operated at higher speeds to provide the required higher outflow rates and pulsation frequencies.

7. To facilitate cleaning the hygiene unit 70 itself, an additional position of the function selector switch 122 is provided and labelled "Unit". When hygiene unit 70 is turned on by activating main power button 120 and function selector switch 122 is placed in the "Unit" position, the LED indicator corresponding to the step C or clean position on the step selector dial begins flashing. The clean position on step selector dial 124 allows a cleaning solution of one percent benzalkonium chloride aqueous solution (one percent zephiran solution) to be flushed through all fluid containing reservoirs, lines, hoses and nozzles of the hygiene unit. This cleaning of the hygiene unit is completed by subseuently flowing clean tap water through all the fluid containing portions of the unit.

To begin step C, the step selector dial is turned to the step C position, microprocessor 126 receives this information and causes the indicator for step C to glow constantly, indicating the initiation of step C. As step C is initiated, the microprocessor signals the Y valve 94 to open the outflow from the cleansing solution reservoir 82 and close the outflow from water reservoir 80. Subsequently, the microprocessor completes the power circuit to electric pump motor 128, cuasing it to operate at the highest speed setting, producing a pulsating nozzle outflow at approximatty forty pounds per square inch. The microprocessor, via its integral timing circuit, notes the time that electric pump motor 128 begins operation and interrupts the power circuit to this pump after the appropriate time has elapsed for the outflow of one hundred twenty-five milliliters of one percent zephiran solution from cleansing solution reservoir 82.

The microprocessor subsequently signals the actuator of Y valve 94 to close off the outflow from cleansing solution reservoir 82 and to open the outflow from water reservoir 80. The microprocessor 126, then completes the power circuit to electric pump motor 128, causing it to operate at the highest speed, producing a pulsating nozzle outflow at approximately forty pounds per square inch. As timed and controlled by microprocessor 126, the power circuit to electric pump motor 128 is interrupted after the appropriate time has elapsed for the outflow of five hundred milliliters of one percent zephiran solution from the water reservoir. As microprocessor 126 interrupts the power circuit to electric pump motor 128, the zephiran portion of step C is completed. The power circuit for the steady glow of the indicator for step C is interrupted, causing the LED indicator for step C to go off.

At the completion of step C, the microporcessor initiates a circuit that signals main power button 120 to return to the off position. The hygiene unit's main power circuit is thus interrupted and the entire hygiene unit 70 is turned off.

8. Step C is subsequently repeated, using clean water in both reservoirs 80 and 82 rather than one percent zephiran solution previously used in both reservoirs during step C, described above. The repetition of step C using water in both reservoirs is electronically the same as the process for step C described above.

In summary, the daily peristomal and appliance cleansing methods used in conjunction with the cleansing equipment of the present invention provide urostomates with improved hygiene, greater opportunity for the prevention of infection, and additional convenience.

From the foregoing detailed descriptions, it will be evident that there are a number of changes, adaptions, and modifications of the present invention which comes within the province of those persons having ordinary skill in the art to which the aforementioned invention pertains. However, it is intended that all such variations not departing from the spirit of the invention be considered as within the scope thereof as limited by the appended claims.

I claim:

1. A stoma hygiene unit for serially cleansing a stoma faceplate and a receptacle comprising:
   a single fluid pump means,
   a controlling means including a microprocessor means connected to said fluid pump for controlling the operation of said pump,
   a water reservoir operatively connected to said single fluid pump means,
   a cleansing solution reservoir operatively connected to said single fluid pump means,
   a nozzle means operatively connected to said fluid pump means, and
   a valve means for selectively connecting either said water reservoir or said cleansing solution reservoir with said nozzle means,
   wherein said microprocessor means provides sequential control of predetermined differing flow rates and differing cycle times for repeated operation of said single fluid pump to pump means fluid from either the said water reservoir or the said cleansing solution reservoir as selected by said microprocessor means out through said nozzle means to serially cleanse said stoma faceplate and said receptacle.

2. The unit of claim 1 including,
said valve means comprising a Y valve having a first leg connected to said water reservoir, a second leg connected to said cleansing solution reservoir and a third leg connected to said nozzle means with said fluid pump means interposed between this third leg and said nozzle means.

3. The unit of claim 1 including,
said controlling means being adapted to selectively cause fluid to be pumped at either a constant intensity flow or a pulsating flow.

4. The unit of claim 1 including,
said controlling means including an electric motor connected to said pump means.

5. The unit of claim 1 including,
said microprocessor means including means to interrupt the power circuit to said single pump means and providing control according to a predetermined sequence.

6. The unit of claim 5 wherein,
said microprocessor means includes:
means for sensing the position of said valve means and, if not open to said water reservoir, signalling said valve means to open said water reservoir so that fluid flows from said water reservoir to said nozzle means, and
instructing means in said microprocessor means for instructing said controlling means to have said pump means causes the flow of water from said water reservoir at a first rate until a first volume of water has flowed, and
thereafter, said valve means closing off the outflow from said water reservoir and open the outflow from said cleansing solution reservoir, and
said instructing means further instructing said controlling means to have said pump means cause the flow of cleansing solution at a second rate until a second volume of cleaning solution was flowed,
after the passage of a first period of time from the completion of the flow of said second volume, said valve means closing off the outflow from said cleansing reservoir and open the outflow from said water reservoir, and
thereafter, said instructing means further instructing said controlling means to have said fluid pump means causes the flow of water from said water reservoir at a third rate until a third volume of water has flowed.

7. The unit of claim 6 including,
said first rate being a constant flow of approximately fifteen psi,
said first volume being approximately 500 milliliters,
said second rate being a pulsating flow of approximately twenty psi with a frequency of two to four cycles per second,
said second volume being approximately 125 milliliters,
sid first period of time being five minutes,
said third rate being a pulsating flow of approximately twenty psi with a frequency of two to four cycles per second, and
said third volume being approximately 500 milliliters.

8. The unit of claim 5 wherein,
said microprocessor means includes,
means for sensing the position of said valve means and, if not open to said water reservoir, signalling said valve means to open to said water reservoir so that fluid flows from said water reservoir to said nozzle means,
instructing means in said microprocessor means for instructing said controlling means to have said pump means cause the flow of water from said water reservoir at a fourth rate until a fourth volume of water has flowed, and
thereafter, said valve means closing off the outflow from said water reservoir and open the outflow from said cleansing solution reservoir, and
said instructing means further instructing said controlling means to have said pump means cause the flow of cleansing solution at a fifth rate until a fifth volume of cleansing solution has flowed,
after the passage of a second period of time from the completion of the flow of said fifth volume, said valve means closing off the outflow from said cleansing solution reservoir and opening the outflow from said water reservoir, and
thereafter, said instructing means further instructing said controlling means to have said pump means cause the flow of water from said water reservoir at a sixth rate until a sixth volume of water has flowed.

9. The unit of claim 8 including,
said fourth rate being a pulsating flow at approximately forty psi with a frequency of four cycles per second,
said fourth volume being approximately 500 milliliters.
said fifth rate being a pulsating flow of approximately forty psi with a frequency of four cycles per second,
said fifth volume being approximately 125 milliliters,
said second period of time being five minutes,
said sixth rate being a pulsating flow of approximately forty psi with a frequency of four cycles per second, and
said sixth volume being approximately 500 milliliters.

10. The unit of claim 1 including,
said nozzle means including a nozzle handle having a female attachment end.

11. The unit of claim 10 including:
an outflow channel nozzle including an outflow end configured to fit into a faceplate outflow channel extending from the faceplate outer surface to the peristomal area and further including an opposite male connector end adapted to fit and lock into said female attachment end of said nozzle handle.

12. The unit of claim 11 including:
said outflow end including a plurality of peripheral fluid ports,
said outflow channel nozzle including a handle extending between said outflow end and said opposite male connector end at a ten degree angle there between, and
said male connector end comprising a double notch lock means.

13. The unit of claim 10 including,
a receptacle cleansing adapter including an adapter male connector end adapted to fit and lock into said female attachment end of said nozzle handle and further including an opposite male member configured to fit into an opened ostomy receptacle drain valve.

14. The unit of claim 13 including,
said adapter male connector end comprising a double notch means,
said male member comprising a double locking plug seal, and said distal tip of said male member having a plurality of peripheral outflow ports.

15. The unit of claim 10 including,
a urinary drainage system cleansing adapter having a male end adapted to fit and lock into said female attachment end of said nozzle handle comprising a double notch locking means and further having an opposite female connector configured to accomodate the plug or male component of a urinary drainage system connector, comprising a double locking plug seal means.

16. The unit of claim 1 including,
said microprocessor means including means for preventing operation of the unit for a cleansing operation.

17. The unit of claim 16 including,
said safety means including a plurality of operative controller means having each a plurality of operative positions.

18. The unit of claim 17 including,
said operative controller means including,
function selector means and step selector means and power switch means.

19. The unit of claim 18 including,
controller sensing means within said operative controller means for sensing the positions of each of the function selector means and step selector means and said power switch means.

20. The unit of claim 18 including,
said controller sensing means operable to terminate power to said unit in accordance with a predetermination of said microprocessor means whereby a user is made aware of the completion of the units' functions with respect for said serial cleansing.

21. The unit of claim 20 including,
said microprocessor means including means to interrupt the power circuit to said single pump means.

22. A stoma hygiene unit for serially cleansing a stoma faceplate and a receptacle comprising:
a fluid pump means,
a controlling means including a microprocessor means connected to said fluid pump means for controlling the operation of said pump,
a water reservoir operatively connected to said fluid pump means,
a cleansing solution reservoir operatively connected to said fluid pump means,
a nozzle means operatively connected to said fluid pump means, and
a valve means for selectively connecting either said water reservoir or said cleansing solution reservoir with said nozzle means, and
said fluid pump pumping fluid from either the said water reservoir or the said cleansing solution reservoir as selected by said microprocessor means out through said nozzle means,
said microprocessor including safety means for preventing operation of the unit for a cleansing operation,
said safety means including a plurality of operative controller means having each a plurality of operative positions, and
said operative controller means including function selector means for selecting a cleansing function and step selector means for inputting cleansing function steps and power switch means.

23. The unit of claim 21 including,
controller sensing means within said operative controller means for sensing the positions of each of the function selector means and step selector means and said power switch means, and
said controller sensing means operable to terminate power to said unit in accordance with a predetermination of said microprocessor means whereby a user is made aware of the completion of the units' functions with respect for said serial cleansing.

* * * * *